(12) United States Patent
Pedroni

(10) Patent No.: US 6,814,694 B1
(45) Date of Patent: Nov. 9, 2004

(54) DEVICE FOR CARRYING OUT PROTON THERAPY

(75) Inventor: Eros Pedroni, Brugg (CH)

(73) Assignee: Paul Scherrer Institut, Villigen (CH)

( * ) Notice: Subject to any disclaimer, the term of this patent is extended or adjusted under 35 U.S.C. 154(b) by 0 days.

(21) Appl. No.: 10/018,797

(22) PCT Filed: Jun. 20, 2000

(86) PCT No.: PCT/CH00/00334
§ 371 (c)(1),
(2), (4) Date: Apr. 18, 2002

(87) PCT Pub. No.: WO01/00276
PCT Pub. Date: Jan. 4, 2001

(30) Foreign Application Priority Data

Jun. 25, 1999 (CH) .............................................. 1180/99

(51) Int. Cl.[7] .............................................. A61N 5/00
(52) U.S. Cl. .......................................................... 600/1
(58) Field of Search ................................ 600/1–9, 410, 600/411, 414; 250/492.3, 306; 5/601

(56) References Cited

U.S. PATENT DOCUMENTS

| | | | | |
|---|---|---|---|---|
| 4,507,616 A | * | 3/1985 | Blosser et al. ............... | 315/502 |
| 4,870,287 A | * | 9/1989 | Cole et al. ............... | 250/492.3 |
| 5,189,687 A | * | 2/1993 | Bova et al. .................... | 378/65 |
| 5,260,581 A | | 11/1993 | Lesyna et al. | |
| 6,094,760 A | * | 8/2000 | Nonaka et al. ................. | 5/601 |
| 6,207,952 B1 | * | 3/2001 | Kan et al. ................. | 250/252.1 |
| 6,635,882 B1 | * | 10/2003 | Pavlovic et al. ............ | 250/398 |

FOREIGN PATENT DOCUMENTS

| | | |
|---|---|---|
| EP | 0 173 926 | 3/1986 |
| EP | 0 864 337 | 9/1998 |
| EP | 0 911 064 | 4/1999 |
| FR | 2 702 663 | 9/1994 |

OTHER PUBLICATIONS

E. Pedroni et al., "The 200–Me V proton therapy project at the Paul Scherrer Institute: Conceptual Design and Practical Realization", *Med. Phys.* 22, (1), Jan. 1995, pp. 37–53.
International Search Report, PCT/CH00/00334, Dec. 11, 2000.

* cited by examiner

*Primary Examiner*—Samuel G. Gilbert
(74) *Attorney, Agent, or Firm*—Jacob Eisenberg; Paul Scherrer Inst.

(57) ABSTRACT

An apparatus for carrying out proton therapy on a patient comprises a proton beam guiding device using magnets, quadrupoles, and an end-mounted device for proton beam guiding and control device with an exit window for guiding or directing the proton beam to the treatment spot in the patient. A patient table of the apparatus can be moved in a controlled manner in such a way that the patient can be placed in a desired position with respect to the proton beam. The proton beam guiding and controlling device can be turnably or rotatably mounted around a horizontal axis of rotation in such a way that the patient table which is arranged approximately on the plane of the axis of rotation remains accessible from one side at all moments for the person treating the patient. The patient table can be displaced slightly on a horizontal plane, extending inside of the axis of rotation or parallel thereto, about an axis which runs approximately through the isocenter of the device, wherein the isocenter is formed by the intersection of the proton beam with the axis of rotation or the approximate point where the beam intersects with the axis of rotation. The apparatus is particularly suitable for use in the destruction of a sick organ or tumor in the human body.

13 Claims, 4 Drawing Sheets

US 6,814,694 B1

DEVICE FOR CARRYING OUT PROTON THERAPY

RELATED APPLICATION

This application is a Section 371 filing based on International Application PCT/CH00/00334 filed Jun. 20, 2000, the priority of which is claimed under 35 USC §120. A claim for priority under 35 USC §119 is in turn made to Switzerland Application No. 1180/99, filed Jun. 25, 1999.

FIELD

This invention relates to a device for administering proton therapy to human patients as well as various improvements designed to increase safety, to improve and simplify process control, to enhance patient acceptability, and also to allow the device to be constructed to smaller dimensions; the invention also relates to an application of the device

BACKGROUND

Proton therapy, especially that intended for the treatment of cancers, is becoming increasingly important since it entails significant advantages in comparison with the photon-radiation therapy in widespread use.

Although equipment for administering proton therapy has been known since the mid-fifties in the U.S., up to now such therapies have been utilized worldwide only at a few centers such as research institutions. This circumstance is due first to the fact that proton accelerators required are still quite expensive, and secondly to the fact that the proton therapy equipment necessary for administering an efficient and safe therapy is quite large and complex. The first and only purely hospital-based proton therapy device is located in the U.S. at the Loma Linda University Medical Center in California. Additional units are in the process of being put into operation in Boston (U.S.) and Kashiwa (Japan).

Unlike the above device at the Loma Linda University Medical Center in which the proton therapy is performed using a so-called scattering method, a proton therapy device was developed at the Paul Scherrer Institute in Wülingen, Switzerland, which utilizes the so-called spot-scanning method. In this connection, reference is made to the article by Eros Pedroni et al. in Med. Phys. 22 (1), January 1995, pages 37–53 with the title "The 200-Mev Proton Therapy Project at the Paul Scherrer Institute: Conceptual Design and Practical Realization." This article refers to the fundamental principle of the above-mentioned spot-scanning method and to a device described using the term "gantry," with which device proton therapy has now been administered to patients for about three years. Although the outside dimensions of the device at the Paul Scherrer Institute were able to be reduced relative to the device at the Loma Linda University Medical Center by using the so-called spot-scanning method, this device still has a diameter of about 4 m, and has the additional disadvantage that access to patients during treatment is unsatisfactory. A detailed description of the device at the Paul Scherrer Institute may be dispensed with by citing the above reference in the literature, which reference is an integral part of the present patent application.

In European Patent Applications EP 0 864 337 and EP 0 911064, similar arrangements for treating a patient by proton therapy are described, which are partially based on the device developed at the Paul Scherfer Institute or describe similar or the same treatment methods.

The preferred position for a patient is the supine position so as to preclude any deformation of the organs during treatment. Therapy must therefore allow accessibility from all sides and encompass the entire human body; for this reason, the generally known proton therapy devices, including that at the Paul Scherrer Institute, are designed so that the entire proton beam guiding device housing is rotatable 360° about a central axis around the so-called patient table, with the result that the device may have a diameter of between 4 and 12 meters. Especially when treating a patient from below, the proton beam guiding device must be moved under the patient table, or the patient table must be raised to a position several meters above the actual level of the working base. The resulting specific disadvantages may also be found in the above-cited literature reference on page 49 in chapter IV, D4 which cites the problems entailed by raising the patient table in this way. This positioning process is critical, and in the event the device experiences an accident during treatment, a special crane device is required to extract or manage the patient. While this disadvantage may be alleviated by providing a relatively deep shaft under the patient table, this approach creates a risk of accidents, such as the person treating the patient falling Into this shaft.

SUMMARY

The object of this invention is thus to propose measures by which the operation of proton therapy may be simplified and made safer, and in which preferably the outside dimensions of the device may be reduced. This object is achieved by the proton therapy device or apparatus of the invention, and by means of a method for treating a patient according to the invention using the proton therapy apparatus.

The invention proposes that a proton beam guiding and control device, or a proton beam guiding device housing located in the treatment arrangement, not be rotatable by a full 360° around a patient table, unlike the "gantry" of the Paul Scherrer Institute, described in the literature, but that the rotational movement be limited to approximately 270°. Here the rotation occurs essentially about a horizontal axis of rotation, in which axis of rotation generally a controllably movable patient table is located in the starting position. This limitation to 270° results in a region through which the beam guiding and control device is not freely movable, in which region the patient table is freely movable and always readily accessible. It is this accessibility to the patient table in particular which represents an essential improvement provided by this invention since the person providing treatment may always access the patient without danger or obstruction.

The result of this preferred arrangement of the proton beam guiding and control device in which the device is rotatable starting from the horizontal plane running essentially through the axis of rotation both upwards and downwards by approximately 135° about the axis of rotation, or from −90° to +180° from the vertical, is that the patient table is readily accessible from the opposite side. The patient table is thus freely movable within the above-mentioned horizontal plane or within a horizontal plane designed to run nearly parallel to this plane—for example, specifically rotatable by at least 180° about an axis which runs essentially through the isocenter of the proton beam guiding and control device. The isocenter is formed on the one hand by the proton beam exiting the proton beam guiding and control device, and on the other hand by the axis of rotation about which this device is rotatable.

The result of this arrangement according to the invention is first of all, as already mentioned, that the patient table is always readily accessible, and secondly that despite this accessibility treatment of the patient from all sides is possible since first of all treatment both from above and below is ensured, as is treatment from both sides, the treatment being enabled by rotating the patient table by 180°.

Preferred variant embodiments of the arrangement according to the invention are characterized in the dependent claims.

To provide a fuller understanding of the invention, an example of a proton beam treatment device according to the invention is described in more detail based on FIGS. 1–3.

DETAILED DESCRIPTION

Figure 1:
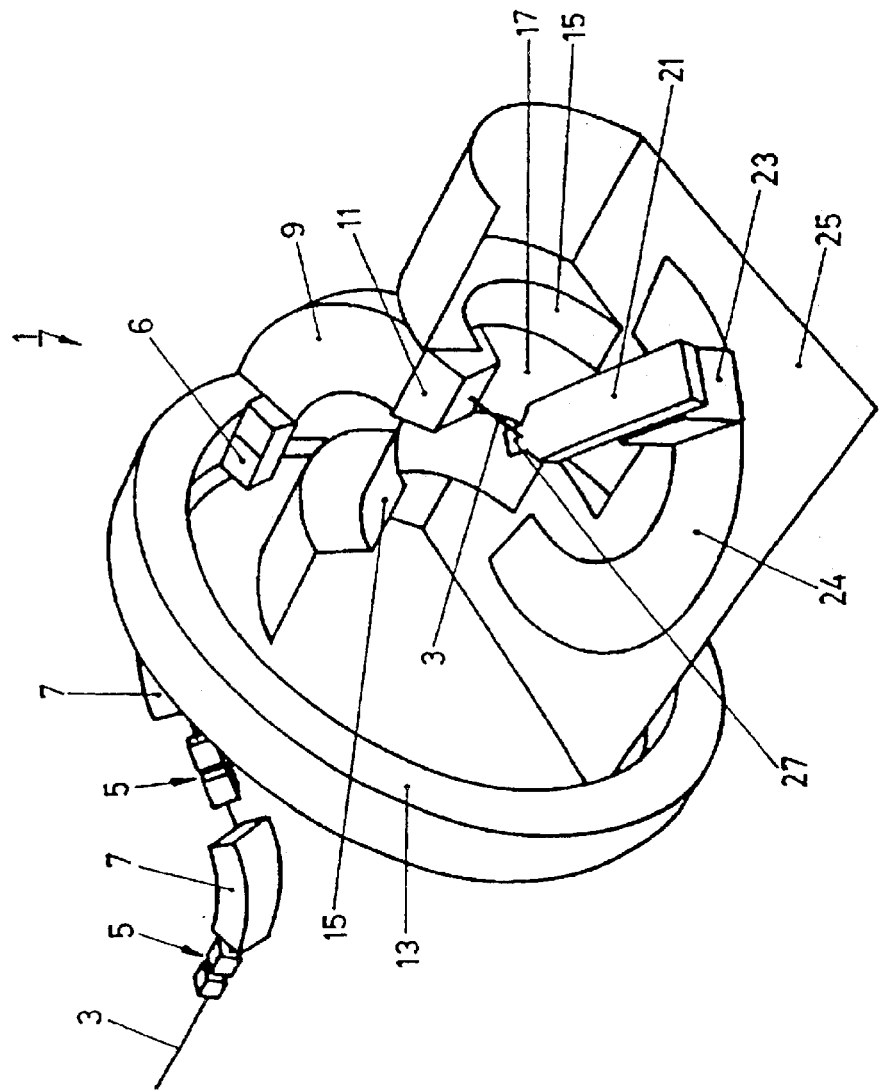
FIG. 1 is a perspective view of a proton beam treatment device for treatment of a patient from the side.

FIG. 1 shows in schematic and simplified form a device or apparatus 1 for treating a patient using proton beam therapy. Here the proton beam 3 is directed by quadrupoles 5 and magnets 7 to the actual end-mounted proton beam guiding and control device 9. Located on the front face of this proton beam guiding and control device is an exit window 11 or so-called "nozzle" through which the proton beam exits and is directed to the patient. The proton beam may be deflected horizontally within a narrowly limited angle by an additional deflection magnet arrangement 6, also called a "sweeper magnet." At the same location, the drawings show a second "sweeper magnet" which may be used as an option to effect a rapid magnetic motion of the beam—but one which is limited by the aperture of the 90° magnet. Also located in the region of exit window 11 and not visible in FIG. 1 is a penetration depth adjustment device, also called a "range shifter," by which the penetration depth of the proton beam into the body of the patient may be set. It is important here to again refer to the article by Pedroni et al. cited in the preamble which describes the basic principles of operation for a proton beam therapy device such as the so-called "gantry" at the Paul Scherrer Institute.

Also shown in FIG. 1 is a guide rail 13 on which is arranged the proton beam guiding and control device 9 so as to be movable about a central axis of rotation. Protruding through lateral shielding guides 15, the exit window 11 moves in a slit-like opening 17 along mounting device 13 when the guiding and control device (9) is moved.

A patient table 21 is arranged to lie in a horizontal plane, running essentially through the axis of rotation of the guiding and control device. This table is movable about an axis of rotation and on a mounting device 23 along a guide 24, this guide being located on a working platform 25. The rotation of patient table 21 proceeds preferably here about an axis of rotation which runs essentially through the head region 27 of patient table 21, and which axis of rotation runs mainly through the region of the so-called isocenter of the device. It is of course possible to have the horizontal plane in which the patient table 21 is located also run parallel a certain distance above or below the horizontal plane through which the rotational axis of proton beam guiding and control device 9 runs. This distance should be restricted, however, so as to ensure that proper treatment is possible from above and below, and additionally to allow the patient table to be capable of being accessed at a suitable height from working platform 25 by the person providing treatment. It is of course also possible to have patient table 21 be arranged on mounting device 23 so as to be both adjustable vertically and slidable in the longitudinal and transverse axes of the table.

The rotatability of the patient table should encompass an angle of at least 180°, although it is clearly evident from FIG. 1 that an angle greater than 180° is not feasible for reasons of design and is also not necessary. According to another special variant embodiment, it is also possible to design the patient table to be rotatable about another axis of rotation, for example, around a vertical axis of rotation running through the center of the table. This rotation is necessary or useful, for example, when a patient is to be treated in the leg region and this region must thus be aligned with the isocenter of the device to allow, for example, a tumor in one leg to be treated accordingly by the proton beam.

Figure 2:
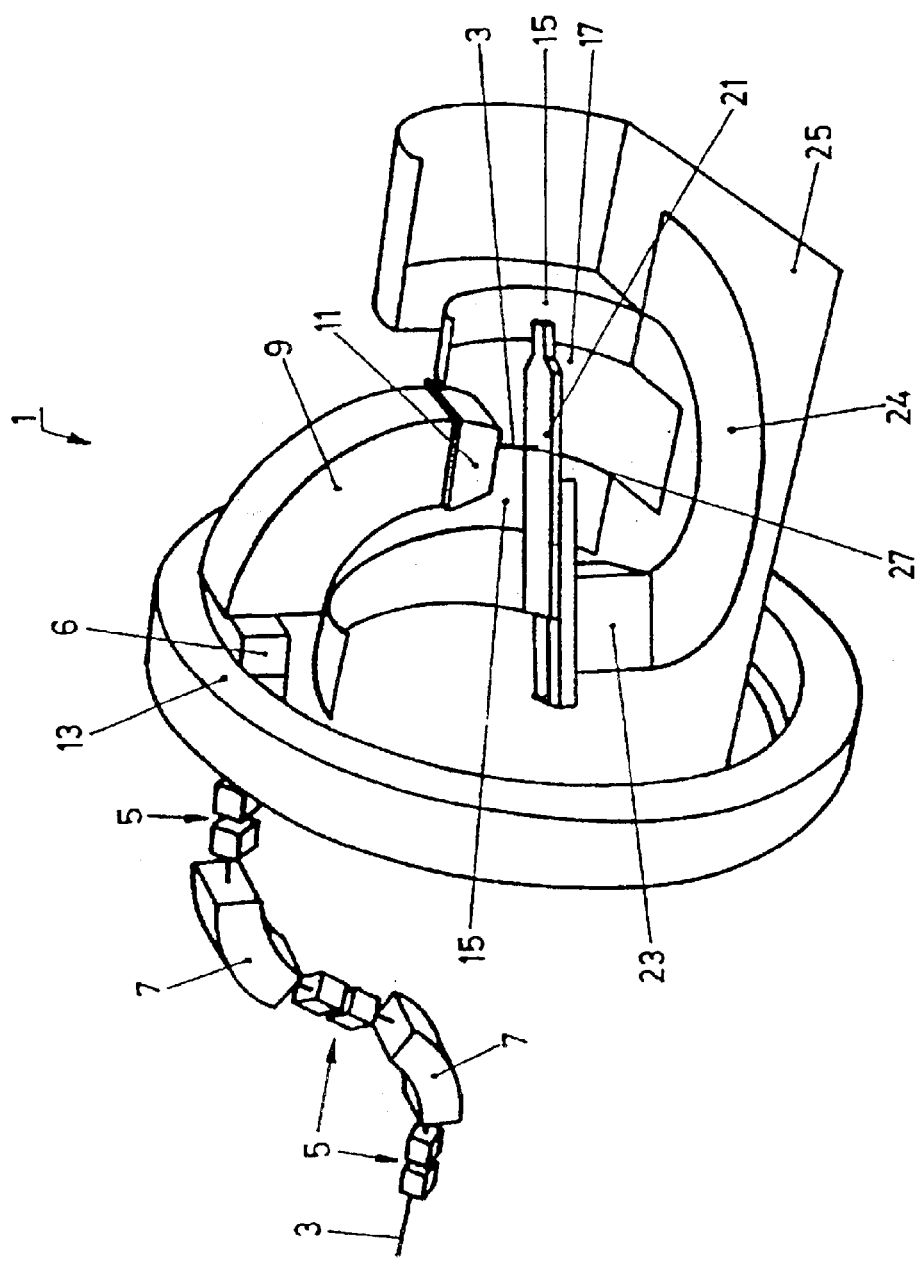
FIG. 2 shows the device in FIG. 1 for treatment of a patient from above.

FIG. 2 shows the same device as in FIG. 1 with beam guiding and control device 9 in the top orientation. In other words, in the arrangement of FIG. 2 the proton beam treatment is administered from above, while in addition the patient table is in a position different from that in FIG. 1. In addition, FIG. 2 clearly shows that the patient table is slidable in the longitudinal axis of the table.

Figure 3:
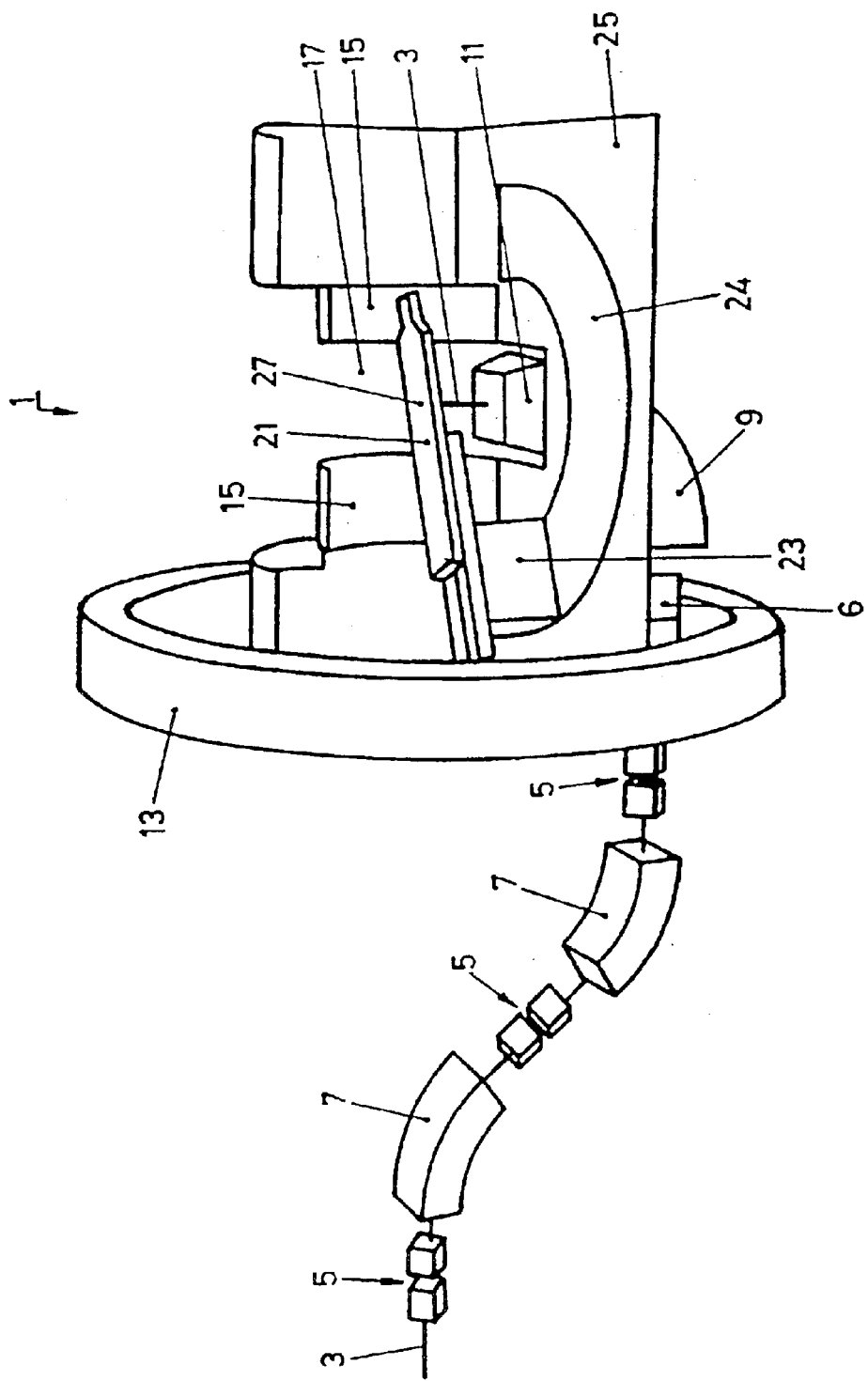
FIG. 3 shows the device in FIG. 1 for treatment of a patient from below.

Finally FIG. 3 shows yet another position attainable by beam guiding and control device 9 where treatment of the patient is administered from below.

The fundamental advantage of the device described according to the invention over the known "gantry" at the Paul Scherrer Institute is immediately evident in the fact that the patient table, for example, does not need to be raised significantly to administer treatments from below and that as a consequence accessibility to the patient table for the person providing treatment is always ensured. This feature has advantages not only for a patient receiving treatment but also for a person providing treatment since with the device according to the invention there is no longer any risk of accidentally falling into a shaft.

An additional problem associated with existing proton treatment devices is encountered in the region of the exit window of the proton beam housing, also called the "nozzle" in English and in technical parlance. Located in the region of this exit window in the device described in the introduction above is a penetration depth adjustment device, also called a "range shifter" with which the penetration depth of the proton beam is controlled very precisely since the energy required to destroy a malignant organ or tumor is released precisely at the end of the range of the proton beam.

In practice it has been found that the proton beam is disturbed by the air gap between the so-called "range shifter" and the patient, thereby degrading the precision of beam control at least slightly.

Figure 4:
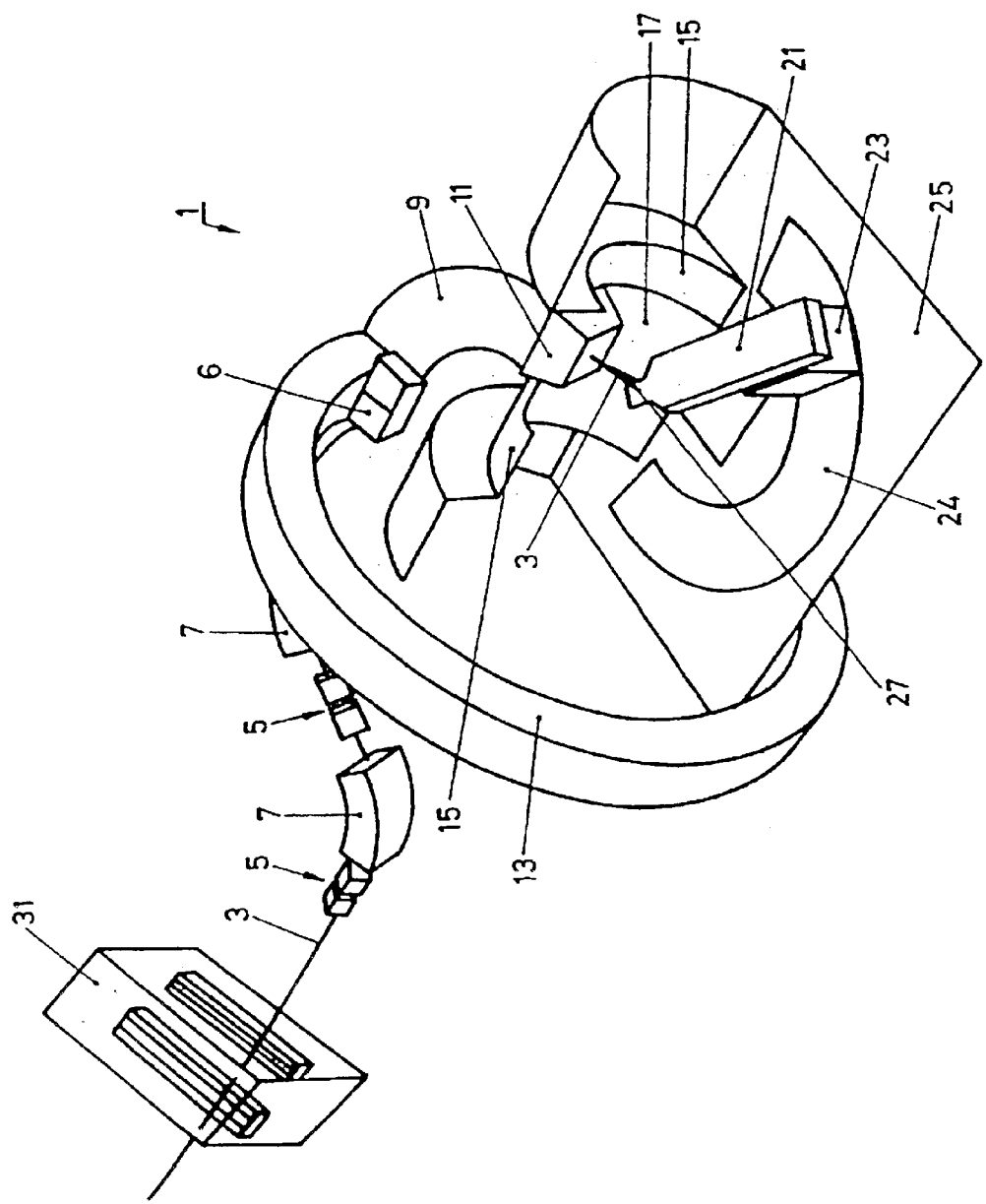
FIG. 4 depicts a schematic representation of the proton beam treatment device with the range shifter located before the treatment arrangement.

For this reason, the invention also proposes locating this adjustment device for modifying the range of the proton beam, or the so-called "range shifter," no longer in the region of the output window or the so-called "nozzle" on the proton beam guiding housing, but instead before the entry of the proton beam into the guiding housing in which the proton beam is guided, in known fashion, to the patient and to the so-called "spot" receiving treatment. With respect to FIG. 1, this means that the so-called "range shifter" is no longer located in the region of exit window 11 but placed before the treatment arrangement 1, as FIG. 4 shows schematically, specifically with reference number 31.

Placing the so-called "range shifter" before the following proton beam guiding device within the treatment arrangement does, however, have the effect that in conjunction with this design magnetic arrangements 7, or the magnet arrangement in the end-mounted proton beam guiding and control device housing 9, must be made variable in order to compensate for an increased or attenuated energy of the proton beam so that the proton beam may ultimately be in turn directed to the desired spot in the patient. However, this is no problem using the currently known process controls or known computer controls, while on the other hand the above-cited problems connected with the precision of beam control may be significantly improved by simplifying the design of the exit window.

The usual procedure for the required destruction of the malignant cells in an organ or in a human body is to move the patient table relative to the proton beam guiding housing in discrete steps so as to allow the proton beam to scan the entire region in the organ or human body point by point. This motion of the patient table is necessary since the "sweeper magnet" and "range shifter" move the proton beam only in two directions, or two-dimensionally, so that the patient table must be designed to be movable to accommodate the spatial treatment of a region in a patient, or to accommodate the third dimension. With the selected spot-scanning method, this motion of the patient table is not continuous but occurs, as mentioned, in discrete steps. This discrete motion is often viewed as disadvantageous or awkward, especially by the attending physicians or persons providing treatment.

For this reason, another variant embodiment of the proton therapy device according to the invention proposes a covering housing in the region of the exit window or so-called "nozzle" in which all the devices required for dosing and control or shielding, and elements for controlling the proton beam, are located out of sight. With respect to the motion, this housing itself is coupled to the patient table through a control device such that the discrete movements of the table are also effected by this covering housing and for the patient no relative motion with respect to the proton beam guiding housing occurs. An additional advantage of including such a covering housing is the fact that the relative position of a contact-hazard-protection device, which may be integrated with the housing, always ensures optimum protection in the event the patient table is to be moved relative to the exit window or the "nozzle." Such a protection device may thus be located within the housing where it can interrupt the proton beam within fractions of a millisecond.

The advantage of including such a covering housing is also the fact that, for example, the collimators and compensators required for concentrating and focusing the proton beam in other known devices, for example, those using the so-called scattering method, may be located in such a housing. The controlled coupling of the covering with the patient table ensures in this case that even when the patient table is moved the proton beam always remains directed at the proper spot in the body of the patient body.

With respect to FIG. 1, this means that the housing 11 of the exit window, shown schematically, is not attached to proton beam guiding and control device 9 but is controlled to move also synchronously with the movements of the patient table. It is possible here to couple the movements of covering housing 11 with those of patient table 21 by using a control device so that no relative motions between the housing and the table take place when patient table 21 is moved during treatment of the patient.

The improvements proposed according to the invention for a proton beam treatment device, especially one utilizing the spot-scanning method such as the so-called "gantry" at the Paul Scherrer Institute, result in significant simplifications in the operation of the device as well as enhancements in the safety and user acceptability of the device, both for patients as well as for the operating personnel.

What is claimed is:

1. An apparatus for treating a patient using proton therapy, comprising:

a proton beam guiding device employing magnets, quadrupoles, and an end-mounted proton beam guiding and control device with an exit window for guiding or directing the proton beam to the treatment spot in the patient;

a controllably movable patient table for moving the patient to the desired position relative to the proton beam, said table positioned over an immobile floor;

wherein the proton beam guiding and control device is located so as to be turnable or rotatable by turning or rotating less than a fill 360° about a horizontal axis in such a way that there results a region through which the proton beam guiding and control device is not freely movable, in which region the patient table located in essentially the plane of the horizontal axis of rotation remains accessible from the side and the beam guiding and control device is arranged to be turnable or rotatable by at least 135° upwards and downwards from a horizontal plane running essentially through the horizontal axis of rotation; and wherein the patient table is rotatable in a horizontal plane running essentially through the axis of rotation of the proton beam guiding device or parallel to it and displaced by a small deviation around an axis which runs essentially through the isocenter of the apparatus, which isocenter is formed by the intersection of the proton beam with the horizontal axis of rotation or with the intersection by approximation of the beam with the horizontal axis of rotation.

2. Apparatus according to claim 1, wherein the beam guiding and control device is arranged to be rotatable about the horizontal axis of rotation from a vertical plane running essentially through the horizontal axis of rotation by an angle of 90° from the side of the vertical plane on which the patient table is located up to an angle of approximately 180° on the opposite side of the vertical plane.

3. Apparatus according to claim 1, wherein the patient table is arranged to be rotatable or movable in the region of the horizontal plane through which the beam guiding and control device is not movable, or which region lies opposite another region through which the beam guiding and control device is movable.

4. Apparatus according to claim 1, wherein the patient table is rotatable about an axis in an end-mounted region an the patient table.

5. Apparatus according to claim 1, wherein the patient table is arranged to be slidable or movable in its longitudinal axis.

6. Apparatus according to claim 1, wherein the patient table is designed to be additionally rotatable about an axis running vertically in essentially the center region of the table, to be movable in a direction transverse to the longitudinal axis, and also to be adjustable in height.

7. Apparatus according to claim 1, further comprising a proton beam penetration depth adjustment device located in front of the apparatus before the magnets and quadrupoles, the proton beam penetration depth adjustment device comprising a system of plates or blades movable in or through the proton beam so as to control or restrict the energy and the associated penetration depth of the proton beam in the patient.

8. Apparatus for treating a patient using proton therapy, comprising:

a proton bean guiding device employing magnets, quadrupoles, and an end-mounted proton beam guiding and control device with an exit window for directing the proton beam to the treatment spot in the patient;

a controllably movable patient table for moving the patient to the desired position relative to the proton bean;

wherein the exit window or a covering housing which is end-mounted on the proton beam guiding and control device and forms the exit window, is provided which is movement-coupled with the patient table during treatment such that during treatment of the patient discrete movements effected by the patient table are synchronously reproduced by the exit window or covering housing.

9. Apparatus according to claim 8, further comprising an additional control device for coupling the motion of the patient table with the exit window or covering housing during treatment of a patient.

10. A method for treating a patient using proton therapy, the method comprising:

directing a proton beam to a treatment spot in a patient using an apparatus comprising a proton beam guiding device employing magnets, quadrupoles, and an end-mounted proton beam guiding and control device with an exit window for guiding or directing the proton beam to the treatment spot in the patient, wherein the proton beam guiding and control device is located so as to be tunable or rotatable by turning or rotating less than a full 360° about a horizontal axis in such a way that there results a region through which the proton beam guiding and control device is not freely movable; and a controllable movable patient table positioned over an immobile floor for moving the patient to the desired position relative to the proton beam and the guiding and control device is arranged to be turnable or rotatable by at least 135° upwards and downwards from a horizontal plane running essentially through the horizontal axis of rotation; and wherein the method includes positioning a person lying on the patient table by moving the patient table and proton beam guiding and control device of the apparatus such that the proton beam is directed to the treatment spot in the patient, and wherein the patient table remains accessible by way of said region at all times from one side.

11. The method according to claim 10, wherein the moving includes positioning the proton beam guiding and control device and the patient table around one axis—the proton beam guiding and control device by turning or rotation about a horizontal axis of rotation and the patient table by turning in a horizontal plane running essentially through the horizontal axis of rotation or parallel to this and arranged so as to be displaced by small deviation—which one axis runs essentially through the isocenter of the apparatus, which isocenter is formed by the intersection of the proton beam with the axis of rotation or with the intersection by approximation of the beam with the axis of rotation.

12. The method according to claim 10, further comprising controlling or restricting the energy, and associated with this, the penetration depth of the proton beam in the patient by means of a proton beam penetration adjustment device located in front of the apparatus before the magnets and quadrupoles, which adjustment device comprises a system of plates or blades movable in or through the proton beam.

13. The method according to claim 10, wherein the treating includes destroying a malignant organ or tumor in a human body.

* * * * *